(12) United States Patent
Adams et al.

(10) Patent No.: US 9,993,292 B2
(45) Date of Patent: Jun. 12, 2018

(54) SHOCK WAVE BALLOON CATHETER WITH MULTIPLE SHOCK WAVE SOURCES

(71) Applicant: SHOCKWAVE MEDICAL, INC., Fremont, CA (US)

(72) Inventors: John Adams, Snohomish, WA (US); Thomas G. Goff, Mountain View, CA (US); Doug Hakala, Woodinville, WA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 0 days. days.

(21) Appl. No.: 15/474,885

(22) Filed: Mar. 30, 2017

(65) Prior Publication Data
US 2017/0258523 A1 Sep. 14, 2017

Related U.S. Application Data

(63) Continuation of application No. 13/534,658, filed on Jun. 27, 2012, now Pat. No. 9,642,673.

(51) Int. Cl.
*A61B 18/14* (2006.01)
*A61B 18/00* (2006.01)
(Continued)

(52) U.S. Cl.
CPC .... *A61B 18/1492* (2013.01); *A61B 17/22022* (2013.01); *A61B 18/00* (2013.01);
(Continued)

(58) Field of Classification Search
CPC .......... A61B 17/2202; A61B 17/22022; A61B 17/2251; A61B 17/320725; A61B 17/22029; A61B 2017/22024; A61B 2017/22025; A61B 2017/22058; A61B 2017/22061; A61B 2017/22062;
(Continued)

(56) References Cited

U.S. PATENT DOCUMENTS 3,413,976 A 12/1968 Roze
3,785,382 A 1/1974 Schmidt-Kloiber et al.
(Continued)

FOREIGN PATENT DOCUMENTS

CN 1269708 A 10/2000
CN 102057422 A 5/2011
(Continued)

OTHER PUBLICATIONS

International Search Report and Written Opinion received for PCT Patent Application No. PCT/US2016/060817, dated Feb. 20, 2017, 13 pages.
(Continued)

*Primary Examiner* — Elmer Chao
(74) *Attorney, Agent, or Firm* — Morrison & Foerster LLP

(57) ABSTRACT

An apparatus includes a balloon adapted to be placed adjacent a calcified region of a body. The balloon is inflatable with a liquid. The apparatus further includes a shock wave generator within the balloon that produces shock waves that propagate through the liquid for impinging upon the calcified region adjacent the balloon. The shock wave generator includes a plurality of shock wave sources distributed within the balloon.

9 Claims, 6 Drawing Sheets

(51) Int. Cl.
*A61B 17/22* (2006.01)
*A61B 17/225* (2006.01)
*A61B 17/3207* (2006.01)

(52) U.S. Cl.
CPC ..... *A61B 17/2202* (2013.01); *A61B 17/22029* (2013.01); *A61B 17/2251* (2013.01); *A61B 17/320725* (2013.01); *A61B 2017/22024* (2013.01); *A61B 2017/22025* (2013.01); *A61B 2017/22051* (2013.01); *A61B 2017/22058* (2013.01); *A61B 2017/22061* (2013.01); *A61B 2017/22062* (2013.01); *A61B 2017/22098* (2013.01)

(58) Field of Classification Search
CPC ................ A61B 18/1492; A61B 18/00; A61B 2017/22051; A61B 2017/22098
See application file for complete search history.

(56) References Cited

U.S. PATENT DOCUMENTS

| | | |
|---|---|---|
| 3,902,499 A | 9/1975 | Shene |
| 4,027,674 A | 6/1977 | Tessler et al. |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,900,303 A | 2/1990 | Lemelson |
| 5,009,232 A | 4/1991 | Hassler et al. |
| 5,057,103 A | 10/1991 | Davis |
| 5,057,106 A | 10/1991 | Kasevich et al. |
| 5,078,717 A * | 1/1992 | Parins ............... A61B 18/1492 606/48 |
| 5,103,804 A | 4/1992 | Abele et al. |
| 5,152,767 A | 10/1992 | Sypal et al. |
| 5,152,768 A | 10/1992 | Bhatta |
| 5,176,675 A | 1/1993 | Watson et al. |
| 5,246,447 A | 9/1993 | Rosen et al. |
| 5,281,231 A | 1/1994 | Rosen et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | de la Torre et al. |
| 5,931,805 A | 8/1999 | Brisken |
| 6,007,530 A | 12/1999 | Doernhoefer et al. |
| 6,033,371 A | 3/2000 | Torre et al. |
| 6,083,232 A | 7/2000 | Cox |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,505,812 B1 | 3/2009 | Eggers et al. |
| 7,569,032 B2 | 8/2009 | Naimark et al. |
| 8,556,813 B2 | 10/2013 | Cioanta et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 9,005,216 B2 | 4/2015 | Hakala et al. |
| 9,011,463 B2 | 4/2015 | Adams et al. |
| 9,333,000 B2 | 5/2016 | Hakala et al. |
| 9,433,428 B2 | 9/2016 | Hakala et al. |
| 9,642,673 B2 | 5/2017 | Adams et al. |
| 2001/0044596 A1 | 11/2001 | Jaafar |
| 2002/0045890 A1 | 4/2002 | Brisken et al. |
| 2002/0177889 A1 | 11/2002 | Brisken et al. |
| 2003/0004434 A1 | 1/2003 | Greco et al. |
| 2003/0176873 A1 | 9/2003 | Chemenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0113722 A1 | 5/2005 | Schultheiss |
| 2005/0113822 A1 | 5/2005 | Fuimaono et al. |
| 2005/0228372 A1 | 10/2005 | Truckai et al. |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0184076 A1 | 8/2006 | Gill et al. |
| 2006/0190022 A1 | 8/2006 | Beyar et al. |
| 2007/0016112 A1 | 1/2007 | Schultheiss et al. |
| 2007/0088380 A1 | 4/2007 | Hirszowicz et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0255270 A1 | 11/2007 | Carney |
| 2007/0282301 A1 | 12/2007 | Segalescu et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0203255 A1 | 8/2012 | Hawkins et al. |
| 2012/0221013 A1 | 8/2012 | Hawkins et al. |
| 2013/0030431 A1 | 1/2013 | Adams |
| 2013/0030447 A1 | 1/2013 | Adams |
| 2013/0116714 A1 | 5/2013 | Adams et al. |
| 2013/0150874 A1 | 6/2013 | Kassab |
| 2014/0046229 A1 | 2/2014 | Hawkins et al. |
| 2014/0052147 A1 | 2/2014 | Hakala et al. |
| 2014/0074111 A1 | 3/2014 | Hakala et al. |
| 2015/0238208 A1 | 8/2015 | Adams et al. |
| 2015/0320432 A1 | 11/2015 | Adams et al. |

(56) References Cited

U.S. PATENT DOCUMENTS

| | | | |
|---|---|---|---|
| 2016/0183957 A1 | 6/2016 | Hakala et al. | |
| 2016/0331389 A1 | 11/2016 | Hakala et al. | |
| 2017/0135709 A1 | 5/2017 | Nguyen et al. | |

FOREIGN PATENT DOCUMENTS

| | | | |
|---|---|---|---|
| CN | 102271748 A | 12/2011 | |
| CN | 102355856 A | 2/2012 | |
| CN | 102765785 A | 11/2012 | |
| DE | 3038445 A1 | 5/1982 | |
| DE | 202006014285 U1 | 12/2006 | |
| EP | 0442199 A2 | 8/1991 | |
| EP | 0571306 A1 | 11/1993 | |
| EP | 0647435 A1 | 4/1995 | |
| JP | 62-275446 A | 11/1987 | |
| JP | 6-125915 A | 5/1994 | |
| JP | 7-47135 A | 2/1995 | |
| JP | 10-99444 A | 4/1998 | |
| JP | 10-513379 A | 12/1998 | |
| JP | 2002-538932 A | 11/2002 | |
| JP | 2004-81374 A | 3/2004 | |
| JP | 2005-501597 A | 1/2005 | |
| JP | 2005-95410 A | 4/2005 | |
| JP | 2005-515825 A | 6/2005 | |
| JP | 2006-516465 A | 7/2006 | |
| JP | 2007-532182 A | 11/2007 | |
| JP | 2011-524203 A | 9/2011 | |
| JP | 2012-508042 A | 4/2012 | |
| WO | 1996/024297 A1 | 8/1996 | |
| WO | 1999/000060 A1 | 1/1999 | |
| WO | 1999/002096 A1 | 1/1999 | |
| WO | 2000/056237 A2 | 9/2000 | |
| WO | 2004/069072 A2 | 8/2004 | |
| WO | 2005/099594 A1 | 10/2005 | |
| WO | 2006/127158 A2 | 11/2006 | |
| WO | 2007/149905 A2 | 12/2007 | |
| WO | 2009/121017 A1 | 10/2009 | |
| WO | 2009/152352 A2 | 12/2009 | |
| WO | 2010/014515 A2 | 2/2010 | |
| WO | 2011/094111 A2 | 8/2011 | |
| WO | 2011/143468 A2 | 11/2011 | |
| WO | 2012/025833 A2 | 3/2012 | |
| WO | 2013/059735 A1 | 4/2013 | |
| WO | 2015/017499 A1 | 2/2015 | |

OTHER PUBLICATIONS

Notice of Allowance received for Chinese Patent Application No. 201380033808.3, dated Dec. 29, 2016, 4 pages (See Communication under 37 CFR § 1.98(a) (3)).
Notice of Allowance received for Chinese Patent Application No. 201380041656.1, dated Mar. 3, 2017, 4 pages (See Communication under 37 CFR § 1.98(a) (3)).
Notice of Allowance received for Japanese Patent Application No. 2015-520522, dated Feb. 23, 2017, 3 pages (See Communication under 37 CFR § 1.98(a) (3)).
Notice of Allowance received for U.S. Appl. No. 14/515,130, dated May 2, 2016, 8 pages.
Office Action received for Australian Patent Application No. 2013284490, dated Jun. 5, 2017, 4 pages.
Office Action received for Australian Patent Application No. 2013300176, dated Nov. 10, 2016, 2 pages.
Office Action received for Japanese Patent Application No. 2015-526523, dated Jan. 25, 2017, 8 pages (5 pages of English Translation and 3 pages).
Advisory Action received for U.S. Appl. No. 12/482,995, dated Jun. 2, 2014, 3 pages.
Advisory Action received for U.S. Appl. No. 12/482,995, dated Sep. 29, 2011, 2 pages.
Advisory Action received for U.S. Appl. No. 12/581,295, dated Jul. 3, 2014, 3 pages.
Advisory Action received for U.S. Appl. No. 13/049,199, dated Jun. 7, 2012, 3 pages.
Advisory Action received for U.S. Appl. No. 13/267,383, dated Jan. 6, 2014, 4 pages.
Advisory Action received for U.S. Appl. No. 13/615,107, dated Nov. 6, 2015, 3 pages.
Cleveland et al., "The Physics of Shock Waw Lithotripsy", Extracorporeal Shock Waw Lithotripsy, Part IV, Chapter 38, 2012, pp. 317-332.
Connors et al., "Renal Nerves Mediate Changes in Contralateral Renal Blood Flow after Extracorporeal Shockwave Lithotripsy", Nephron Physiology, vol. 95, 2003, pp. 67-75.
Decision to Grant received for European Patent Application No. 13756766.5, dated May 27, 2016, 2 pages.
Decision to Grant received for Japanese Patent Application No. 2011-513694, dated Oct. 7, 2014, 3 pages.
Extended European Search Report (includes Supplementary European Search Report and Search Opinion) received for European Patent Application No. 09763640.1, dated Oct. 10, 2013, 5 pages.
Extended European Search Report received for European Patent Application No. 13827971.6, dated Apr. 12, 2016, 8 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 13/049,199 dated Aug. 11, 2014, 8 pages.
Final Office Action received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107, dated Sep. 1, 2015, 9 pages.
Final Office Action received for U.S. Appl. No. 13/646,570, dated Dec. 23, 2014, 10 pages.
Final Office Action received for U.S. Appl. No. 14/271,342, dated Feb. 27, 2015, 7 pages.
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Current Hypertension Reports, vol. 14, 2012, pp. 567-572.
Intention to Grant received for European Patent Application No. 13756766.5, dated Jan. 8, 2016, 5 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987, dated Nov. 20, 2014, 11 pages.
International Preliminary Report on Patentability received for PCT Patent Application No. PCT/US2013/048277, dated Jan. 8, 2015, 9 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533, dated Mar. 26, 2015, 10 pages.

(56) References Cited

OTHER PUBLICATIONS

International Search Report and Written Opinion receKed for PCT Patent Application No. PCT/US2013/031805, dated May20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report and Written Opinion received for PCT Patent Application No. PCT/US2015/029088, dated Jul. 16, 2015, 13 pages.
International Search Report received for PCT Patent Application No. PCT/US2009/047070, dated Jan. 19, 2010, 4 pages.
International Search Report received for PCT Patent Application No. PCT/US2012/023172, dated Sep. 28, 2012, 3 pages.
International Written Opinion received for PCT Patent Application No. PCT/US2009/047070, dated Jan. 19, 2010, 5 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
Kodama et al., "Shock Waw-Mediated Molecular Delivery into Cells", Biochimica et Biophysica Acta., vol. 1542, 2002, pp. 186-194.
Lauer et al., "Shock Waw Permeabilization as a New Gene Transfer Method", Gene Therapy, vol. 4, 1997, pp. 710-715.
Non Final Office Action received for U.S. Appl. No. 12/482,995, dated Aug. 13, 2014, 10 pages.
Non Final Office Action received for U.S. Appl. No. 12/482,995, dated Jul. 12, 2013, 11 pages.
Non Final Office Action received for U.S. Appl. No. 13/465,264, dated Oct. 29, 2014, 13 pages.
Non Final Office Action received for U.S. Appl. No. 13/534,658, dated Mar. 11, 2016, 12 pages.
Non Final Office Action received for U.S. Appl. No. 13/646,570, dated Oct. 29, 2014, 10 pages.
Non Final Office Action received for U.S. Appl. No. 14/079,463, dated Mar. 4, 2014, 9 pages.
Non Final Office Action received for U.S. Appl. No. 14/218,858, dated Mar. 30, 2016, 13 pages.
Non Final Office Action received for U.S. Appl. No. 14/515,130, dated Jan. 14, 2016, 16 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 13/049,199, dated Feb. 4, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Notice of Acceptance received for Australian Patent Application No. 2009257368, dated Aug. 28, 2014, 2 pages.
Notice of Allowance received for Canadian Patent Application No. 2,727,429, dated May 26, 2015, 1 page.
Notice of Allowance received for U.S. Appl. No. 12/482,995, dated Dec. 24, 2014, 6 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/465,264, dated May 8, 2015, 7 pages.
Notice of Allowance received for U.S. Appl. No. 13/534,658, dated Jan. 5, 2017, 6 pages.
Notice of Allowance received for U.S. Appl. No. 13/534,658, dated Jan. 18, 2017, 4 pages.
Notice of Allowance received for U.S. Appl. No. 13/615,107, dated Dec. 31, 2015, 10 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 13/957,276, dated Aug. 28, 2015, 9 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,276, dated Feb. 25, 2015, 8 pages.
Notice of Allowance received for U.S. Appl. No. 14/271,342, dated Mar. 13, 2015, 5 pages.
Notice of Allowance received for U.S. Appl. No. 14/515,130, dated May 25, 2016, 3 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Canadian Patent Application No. 2,727,429, dated Apr. 14, 2015, 4 pages.
Office Action received for Chinese Patent Application No. 201380033808.3, dated Jul. 5, 2016, 9 pages.
Office Action received for Chinese Patent Application No. 201380041656.1, dated Jul. 5, 2016, 9 pages.
Office Action received for Chinese Patent Application No. 201380042887.4, dated Aug. 8, 2016, 9 pages.
Office Action received for Japanese Patent Application No. 2011-513694, dated Aug. 27, 2014, 6 pages.
Office Action received for Japanese Patent Application No. 2011-513694, dated Jun. 10, 2014, 4 pages.
Office Action received for Japanese Patent Application No. 2014-158517, dated May 19, 2015, 5 pages.
Rosenschein et al., "Shock-Waw Thrombus Ablation, a New Method for Noninvasive Mechanical Thrombolysis", The American Journal of Cardiology, vol. 70, Nov. 15, 1992, pp. 1358-1361.
U.S. Appl. No. 13/777,807, filed Feb. 26, 2013, titled "Shock Wave Catheter System With Arc Preconditioning".
U.S. Appl. No. 14/218,858, filed Mar. 18, 2014, titled "Shockwave Catheter System With Energy Control".
Zhong et al., "Transient Oscillation of Cavitation Bubbles Near Stone Surface During Electrohydraulic Lithotripsy", Journal of Endourology, vol. 11, No. 1, Feb. 1997, pp. 55-61.

* cited by examiner

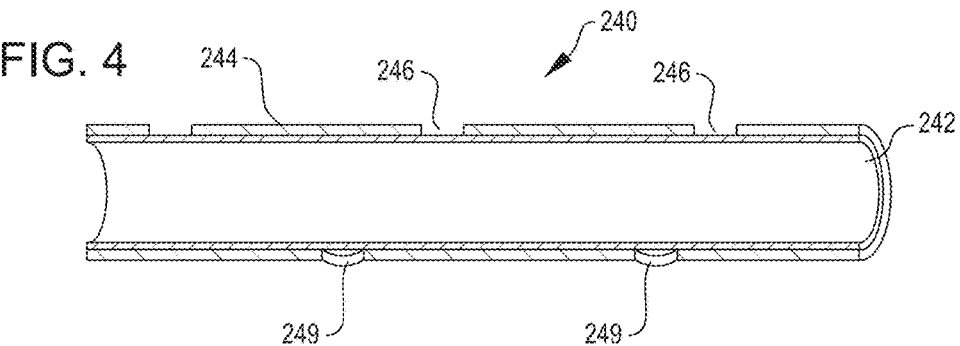
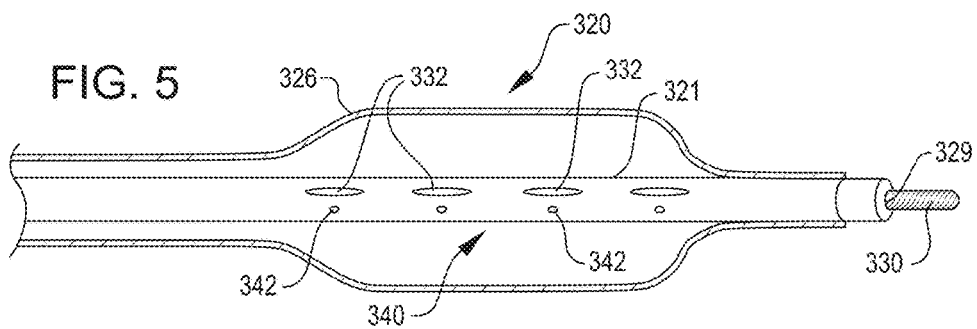
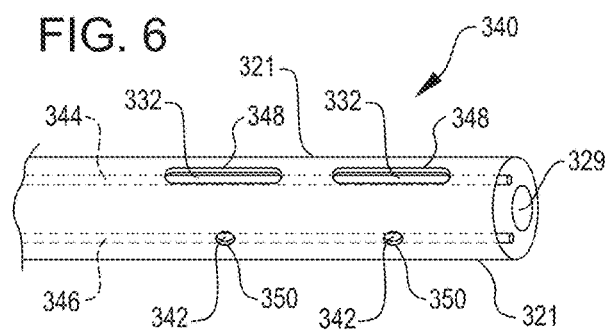
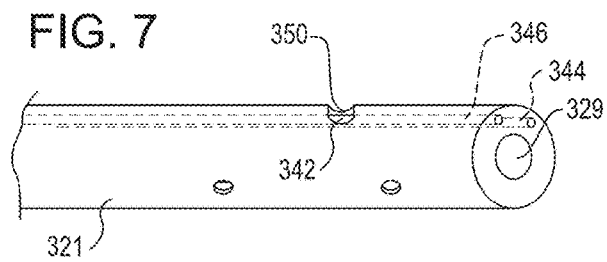

SHOCK WAVE BALLOON CATHETER WITH MULTIPLE SHOCK WAVE SOURCES

CROSS-REFERENCE TO RELATED APPLICATIONS

This application is a continuation of U.S. Ser. No. 13/534,658, filed Jun. 27, 2012, the disclosure of which is incorporated herein by reference in its entirety.

BACKGROUND OF THE INVENTION

Aortic calcification, also called aortic sclerosis, is a buildup of calcium deposits on the aortic valve in the heart. This often results in a heart murmur, which can easily be heard with a stethoscope over the heart. However, aortic calcification usually doesn't significantly affect the function of the aortic valve.

In some cases, though, the calcium deposits thicken and cause narrowing at the opening of the aortic valve. This impairs blood flow through the valve, causing chest pain or a heart attack. Doctors refer to such narrowing as aortic stenosis.

Aortic calcification typically affects older adults. But when it occurs in younger adults, it's often associated with an aortic valve defect that is present at birth (congenital) or with other illnesses such as kidney failure. An ultrasound of the heart (echocardiogram) can determine the severity of aortic calcification and also check for other possible causes of a heart murmur.

At present there is no specific treatment for aortic calcification. General treatment includes the monitoring for further developments of heart disease. Cholesterol levels are also checked to determine the need for medications to lower cholesterol in the hope to prevent progression of aortic calcification. If the valve becomes severely narrowed, aortic valve replacement surgery may be necessary.

The aortic valve area can be opened or enlarged with a balloon catheter (balloon valvuloplasty) which is introduced in much the same way as in cardiac catheterization. With balloon valvuloplasty, the aortic valve area typically increases slightly. Patients with critical aortic stenosis can therefore experience temporary improvement with this procedure. Unfortunately, most of these valves narrow over a six to 18 month period. Therefore, balloon valvuloplasty is useful as a short-term measure to temporarily relieve symptoms in patients who are not candidates for aortic valve replacement.

Patients who require urgent noncardiac surgery, such as a hip replacement, may benefit from aortic valvuloplasty prior to surgery. Valvuloplasty improves heart function and the chances of surviving non-cardiac surgery. Aortic valvuloplasty can also be useful as a bridge to aortic valve replacement in the elderly patient with poorly functioning ventricular muscle. Balloon valvuloplasty may temporarily improve ventricular muscle function, and thus improve surgical survival. Those who respond to valvuloplasty with improvement in ventricular function can be expected to benefit even more from aortic valve replacement. Aortic valvuloplasty in these high risk elderly patients has a similar mortality (5%) and serious complication rate (5%) as aortic valve replacement in surgical candidates.

Transarterial aortic valve replacement is a new procedure where the aortic valve is replaced with a self-expanding nitinol or balloon-expandable valve structure. Such procedures benefit from a smooth non-calcified circumference to attach the new valve. Large calcium deposits may induce leaks around the valve preventing a firm consistent attachment of the valve to the aorta. Thus there is a need for a calcium free valve bed to attach such self-expanding valves.

An alternative method and system for treating stenotic or calcified aortic valves is disclosed and claimed in co-pending U.S. application Ser. No. 12/611,997, filed Nov. 11, 2009 for SHOCKWAVE VALVULOPLASTY SYSTEM. As described therein, a balloon is placed adjacent leaflets of a valve to be treated and is inflatable with a liquid. Within the balloon is a shock wave generator that produces shock waves that propagate through the liquid and impinge upon the valve. The impinging shock waves soften, break and/or loosen the calcified regions for removal or displacement to open the valve or enlarge the valve opening.

The approach mentioned above provides a more tolerable treatment for aortic stenosis and calcified aortic valves than the previously performed aortic valve replacement. It is also a more effective treatment than current valvuloplasty therapy. For patients undergoing transaortic or catheter based aortic valve replacement, this new method can soften, smooth, and open the aortic valve annulus more effectively than current valvuloplasty and prepare the area for a catheter delivered valve.

In the shock wave valvuloplasty described above, the impingement intensity of the shockwaves diminishes as a function of the distance from the shock wave origination point to the valve. More specifically, the impingement intensity of the shock waves is inversely proportional to the square of the distance from the shock wave origination point to the valve. Hence, when applying the shock waves, it would be desirable to maximize their effectiveness by being able to minimize the distance between the shock wave source and the valve location being treated at that moment.

Similar issues are present in angioplasty. There, a calcified region of a vein or artery may extend over some longitudinal distance of the vein or artery. A point shock wave source within an angioplasty balloon, in such instances, would not be uniformly effective across the extent of the calcified region because of the varying distance from the shock wave source to the various portions of the calcified region.

The present invention addresses this and other matters of importance in providing the most efficient and effective valvuloplasty and angioplasty treatment possible.

SUMMARY OF THE INVENTION

In one embodiment, an apparatus comprises a balloon adapted to be placed adjacent a calcified region of a body. The balloon is inflatable with a liquid. The apparatus further includes a shock wave generator within the balloon that produces shock waves that propagate through the liquid for impinging upon the calcified region adjacent the balloon. The shock wave generator includes a plurality of shock wave sources distributed within the balloon, wherein the plurality of shock wave sources are more than two shock wave sources. These shock wave sources can be distributed both longitudinally and circumferentially within the balloon for optimal effect.

The balloon is elongated having a longitudinal dimension along its length and the plurality of shock wave sources extend along a portion of the longitudinal dimension. The balloon has a sidewall and the shock wave sources are in non-touching relation with respect to the balloon sidewall. The shock wave generator may be an electrical arc shock wave generator and the shock wave sources may include a plurality of electrodes. The electrical arc shock wave generator may further include at least one counter electrode adapted to be in contact with the liquid and to receive a voltage polarity opposite a voltage polarity applied to the plurality of electrodes.

The shock wave generator may include an elongated conductor and an insulator overlying the elongated conductor. The insulator may have a plurality of discrete openings, each opening for exposing the elongated conductor to the fluid, to form the plurality of electrodes. An insulated wire may be employed to form the elongated conductor and the overlying insulator.

The apparatus may further include an elongated carrier. The carrier may extend through the balloon and be sealed thereto. The insulated wire may be wrapped about the carrier within the balloon. The carrier may include a guide wire lumen. The insulated wire may be wrapped about the carrier to form electrode coil turns and the apparatus may further include a conductor wire wrapped about the carrier within the balloon and in between the electrode coil turns to form the counter electrode.

The shock wave generator may include an elongated cylindrical conductor and an insulator overlying the elongated cylindrical conductor. The insulator may have a plurality of discrete openings, each opening for exposing the elongated cylindrical conductor to the fluid, to form the plurality of electrodes. The apparatus may further include an elongated carrier extending through the balloon and be in sealed relation thereto. The elongated cylindrical conductor may overlie the carrier within the balloon. The elongated carrier may include a guide wire lumen.

The shock wave generator may be an electrical arc shock wave generator, wherein the shock wave sources include a plurality of electrodes, wherein the apparatus further includes an elongated carrier having a longitudinal dimension extending through the balloon and being in sealed relation thereto, wherein the elongated carrier has a guide wire lumen extending along at least a portion of the longitudinal dimension of the elongated carrier, and wherein at least some of the plurality of electrodes are distributed along the elongated carrier within the balloon.

The elongated carrier may be formed of an insulating material. The shock wave generator may include at least one conductor extending within the elongated carrier in spaced apart relation to the guide wire lumen and along at least a portion of the longitudinal dimension of the elongated carrier and a plurality of discrete portions of the elongated carrier insulating material are removed to expose corresponding portions of the at least one conductor to form the at least some of the plurality of electrodes. At least some of the removed discrete portions of the elongated carrier insulating material may contain a conductive filling. The conductive fillings may be conductively secured to the elongated conductor.

The elongated carrier may be formed of an insulating material. The shock wave generator may include at least first and second elongated conductors extending within the elongated carrier in spaced apart relation to each other and the guide wire lumen and along at least a portion of the longitudinal dimension of the elongated carrier. A plurality of discrete portions of the elongated carrier insulating material may be removed to expose corresponding portions of the at least first and second conductors to form the at least some of the plurality of electrodes.

The removed discrete portions of the elongated carrier insulating material that expose corresponding portions of one of the at least first and second conductors are greater in dimension than the removed discrete portions of the elongated carrier insulating material that expose corresponding portions of another one of the at least first and second conductors. The at least some of the removed discrete portions of the elongated carrier insulating material may contain a conductive filling and at least some of the conductive fillings may be conductively secured to the elongated conductors.

The plurality of electrodes are arranged in series circuit relation. Alternatively the plurality of electrodes are arranged in parallel circuit relation. The apparatus may further include a power source and a multiplexer that selectively couples the power source to the plurality of electrodes, one at a time. In another embodiment, the plurality of electrodes may be arranged in a plurality of series circuit arrangements and the apparatus may further include a multiplexer that selectively couples the power source to the series circuit arrangements, one at a time.

The plurality of shock wave sources may be arranged along a path defining a loop. The balloon may be configured to be placed adjacent leaflets of a valve, the balloon having a first chamber to be adjacent one side of the leaflets and a second chamber to be adjacent an opposite side of the leaflets. The plurality of shock wave sources may be arranged to define a loop of shock wave sources within one of the first and second chambers of the balloon.

The balloon may be configured to be placed adjacent leaflets of a valve, the balloon having a first chamber to be adjacent one side of the leaflets and a second chamber to be adjacent an opposite side of the leaflets, and wherein the plurality of shock wave sources may be arranged to define a first loop of shock wave sources within the first chamber of the balloon and a second loop of shock wave sources within the second chamber of the balloon.

In accordance with another embodiment, an apparatus comprises an elongated carrier and a balloon carried on the elongated carrier in sealed relation thereto. The balloon is adapted to be placed adjacent a calcified region of a body and is inflatable with a liquid. The apparatus further includes an electrical arc shock wave generator within the balloon. The electrical arc shock wave generator includes more than two electrodes distributed within the balloon. Each electrode is adapted to produce shock waves that propagate through the liquid for impinging upon the calcified region adjacent the balloon. The apparatus further includes a counter electrode adapted to be in contact with the liquid and to receive a voltage polarity opposite that applied to the more than two electrodes.

In a further embodiment, a method includes the steps of inserting a balloon in a body adjacent a calcified region, inflating the balloon with a liquid to cause the balloon to contact the calcified region, placing, within the balloon, a shock wave generator including more than two shock wave sources and distributing the more than two shock wave sources within the balloon, and causing the shock wave sources to form shock waves that propagate through the liquid and impinge upon the calcified region.

The inserting step may include inserting the balloon into an artery or vein of the body. The balloon may be elongated having a longitudinal dimension and the distributing step may include distributing the shock wave sources along a portion of the longitudinal dimension.

The inserting step may include inserting the balloon into a valve of the body. The distributing step may include distributing the shock wave sources along a path defining a loop.

The balloon may be configured to be placed adjacent leaflets of the valve and to have a first chamber adapted to be adjacent one side of the leaflets and a second chamber adapted to be adjacent an opposite side of the leaflets. The inserting step may include inserting the balloon into the valve with the first chamber adjacent one side of the leaflets and the second chamber adjacent the opposite side of the leaflets. The distributing step may include distributing the shock wave sources along a path defining a loop of shock wave sources within one of the first and second chambers of the balloon.

In a still further embodiment, the balloon is configured to be placed adjacent leaflets of the valve, wherein the balloon has a first chamber to be adjacent one side of the leaflets and a second chamber to be adjacent an opposite side of the leaflets, wherein the inserting step includes inserting the balloon into the valve with the first chamber adjacent one side of the leaflets and the second chamber adjacent the opposite side of the leaflets, and wherein the distributing step includes distributing the shock wave sources to define a first loop of shock wave sources within the first chamber of the balloon and to define a second loop of shock wave sources within the second chamber of the balloon.

The balloon has a sidewall and the distributing step may include distributing the shock wave sources in non-touching relation with respect to the balloon sidewall. The shock wave generator may be an electrical arc shock wave generator, the shock wave sources may include a plurality of electrodes, and the causing step may include applying voltage pulses between the plurality of electrodes and a counter electrode to form the shock waves.

According to a still further embodiment, a method comprises inserting a balloon in a body adjacent a calcified region, inflating the balloon with a liquid to cause the balloon to contact the calcified region, placing, within the balloon, more than two electrodes in non-touching relation to the balloon and adjacent the calcified regions, placing a counter electrode in contact with the liquid, and applying voltage pulses between the more than two electrodes and the counter electrode, wherein the voltage pulses have a first polarity applied to the two or more electrodes and a second polarity applied to the counter electrode causing the more than two electrodes to form shock waves that propagate through the liquid and impinge upon the calcified region.

BRIEF DESCRIPTION OF THE DRAWINGS

The features of the present invention which are believed to be novel are set forth with particularity in the appended claims. The various described embodiments of the invention, together with representative features and advantages thereof, may best be understood by making reference to the following description taken in conjunction with the accompanying drawings, in the several figures of which like reference numerals identify identical elements, and wherein:

FIG. 4 is a partial sectional view illustrating alternative aspects of the electrode structure of FIG. 3 to provide the plurality of shock wave sources;

FIG. 5 is a side view of another dilating angioplasty balloon catheter including a plurality of shock wave sources according to a further embodiment of the invention;

FIG. 6 is a perspective view illustrating a manner in which an electrode structure of the catheter of FIG. 5 may be produced to provide the plurality of shock wave sources according to an embodiment of the invention;

FIG. 7 is another perspective view illustrating another aspect of the electrode structure for the of FIG. 5 according to an embodiment of the invention;

DETAILED DESCRIPTION OF THE INVENTION

Figure 1:
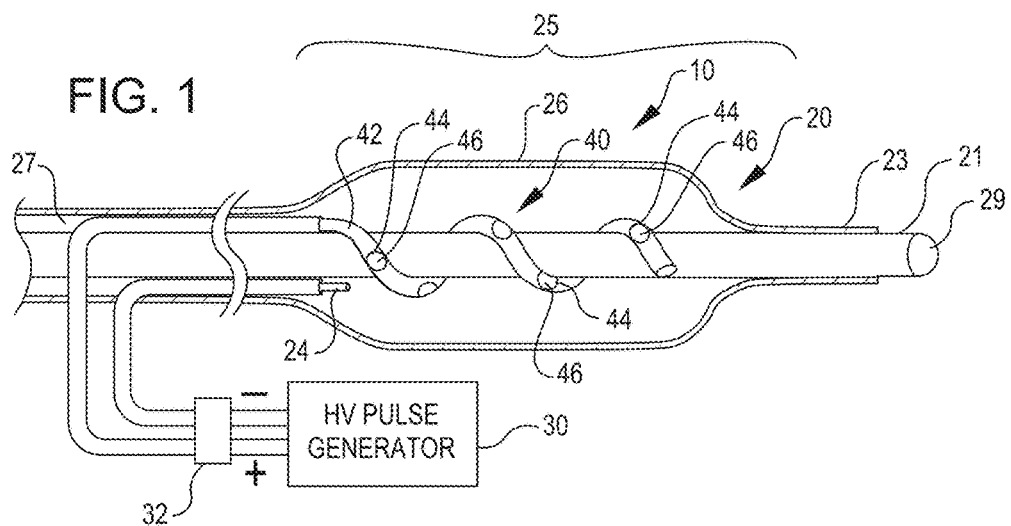
FIG. 1 is a is a simplified drawing of an angioplasty system embodying the invention including a side view of a dilating angioplasty balloon catheter including a plurality of shock wave sources according to one embodiment.

FIG. 1 shows an angioplasty system 10 embodying the invention including a dilating angioplasty balloon catheter 20 including a plurality of shock wave sources according to one embodiment of the invention. The catheter 20 includes an elongated carrier 21, and a dilating balloon 26 formed about the carrier 21 in sealed relation thereto at a seal 23. The balloon 26 forms an annular channel 27 about the carrier 21 through which fluid, such as saline, may be admitted into the balloon to inflate the balloon. The carrier 21 includes a guide wire lumen 29. The guide wire lumen is arranged to receive a guide wire that may be used to direct the catheter to a desired location to locate the balloon adjacent a region of an artery or vein or to treated.

Carried by the carrier 21 is an electrode structure 40. The electrode structure 40 includes an insulated wire 42 wound about the the carrier 21. Within the insulation of the insulated wire 42 are a plurality of openings 44 that expose corresponding discrete portions of the insulated wire conductor to the saline within the balloon. Each opening 44 forms a corresponding shock wave source or electrode 46. As may be see in FIG. 1, a plurality of more than two electrodes are formed in this manner and in non-touching relation to the sidewalls of the balloon 26.

The electrode structure 40 also includes a counter electrode 24. The counter electrode 24 is disposed in non-touching relation to the sidewalls of the balloon 26 and serves as a common electrode to cause an electrical arc to occur between each of the electrodes 46 and the common electrode 24 when a suitable high voltage is applied between the electrodes 46 and the counter electrode 24.

To that end, the electrodes 24 and 46 are attached to a source 30 of high voltage pulses through a connector 32. The electrodes 24 and 46 are formed of metal, such as stainless steel or tungsten, and are placed a controlled distance apart to allow a reproducible arc for a given voltage and current. The electrical arcs between electrode 24 and electrodes 46 in the fluid are used to generate shock waves in the fluid. The variable high voltage pulse generator 30 is used to deliver a stream of pulses across electrode 24 and electrodes 46 to create a stream of shock waves within and along the longitudinal length 25 of the balloon 26 and within the artery being treated (not shown). The magnitude of the shock waves can be controlled by controlling the magnitude of the pulsed voltage, the current, the duration and repetition rate. The insulating nature of the balloon 26 protects the patient from electrical shocks.

The balloon 26 may be filled with water or saline in order to gently fix the balloon in the walls of the artery in the direct proximity with the calcified lesion. The fluid may also contain an x-ray contrast to permit fluoroscopic viewing of the catheter during use. As previously mentioned, the carrier 21 includes a lumen 29 through which a guidewire (not shown) may be inserted to guide the catheter into position. Once the catheter is positioned through use of the guide wire (not shown) and guide wire lumen 29, the physician or operator can start with low energy shock waves and increase the energy as needed to crack the calcified plaque. Such shockwaves will be conducted through the fluid, through the balloon, through the blood and vessel wall to the calcified lesion where the energy will break the hardened plaque without the application of excessive pressure by the balloon on the walls of the artery.

The voltage needed to produce the arcs will depend on the gap between the electrodes and is generally 100 to 3000 volts. The pulse duration will also depend on the surface area of the electrodes 24 and 46 and needs to be sufficient to generate a gas bubble at the surface of the electrodes to cause a plasma arc of electric current to jump each bubble and, upon each occurrence, create a rapidly expanding and collapsing bubble, which creates the mechanical shock wave in the balloon. Such shock waves can be as short as a few microseconds. Both the rapid expansion and the collapse of a bubble create shock waves. The pulse duration can be adjusted to favor one over the other. A large steam bubble will generate a stronger shockwave than a small one. However, more power is needed in the system to generate this large steam bubble. Traditional lithotripters try to generate a large steam bubble to maximize the collapsing bubble's shockwave. Within a balloon such large steam bubbles are less desirable due to the risk of balloon rupture. By adjusting the pulse width to a narrow pulse less than two microseconds or even less than one microsecond, a rapidly expanding steam bubble and shockwave can be generated while at the same time the final size of the steam bubble can be minimized. The short pulse width also reduces the amount of heat in the balloon to improve tissue safety.

Figure 2:
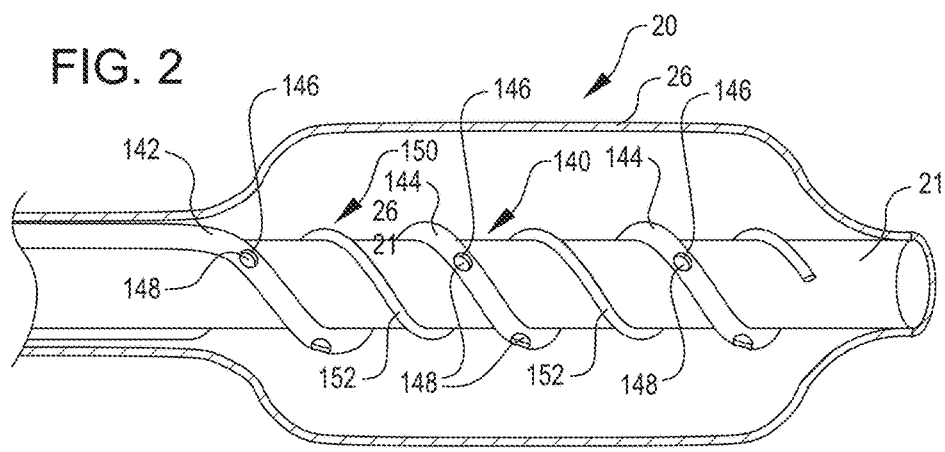
FIG. 2 is a side view of the catheter of FIG. 1 showing an alternate electrode structure that may be employed within the dilating angioplasty balloon catheter of FIG. 1.

FIG. 2 shows another electrode structure 140 that may be employed in the catheter 20 of FIG. 1. Like the electrode structure of FIG. 1, the electrode structure 140 of FIG. 2 includes an insulated wire 142 wound about the the carrier 21 to form electrode coil turns 144. Within the insulation of the insulated wire 142 are a plurality of openings 146 that expose corresponding discrete portions of the insulated wire conductor to the saline within the balloon. Each opening 146 forms a corresponding shock wave source or electrode 148.

The electrode structure 140 further includes a conductor wire wrapped about the carrier 21 within the balloon 26. The conductor wire 150 is wound in between the electrode coil turns 144 to form a counter electrode 152. This provides more uniform spacings between the electrodes 148 and the counter electrode 152. All of the electrodes 148 and 152 are disposed in non-touching relation to the sidewalls of the balloon 26.

Figure 3:
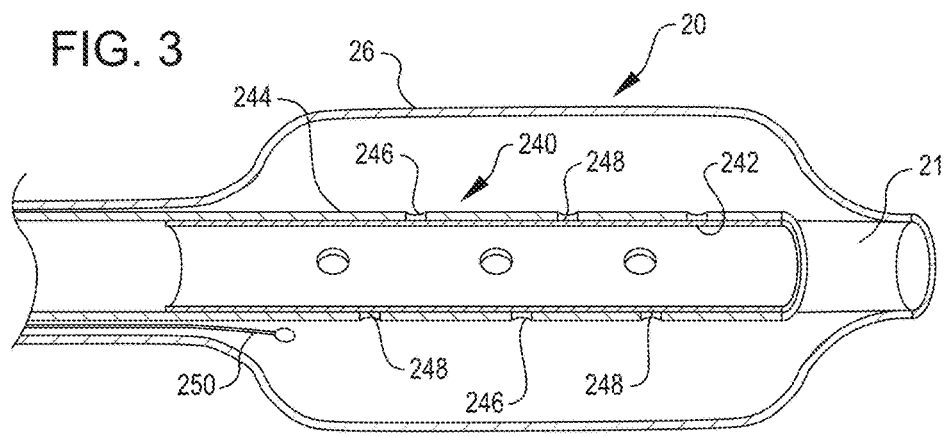
FIG. 3 is a side view of the catheter of FIG. 1 showing still another alternate electrode structure that may be employed within the dilating angioplasty balloon catheter of FIG. 1.

FIG. 3 shows another electrode structure 240 that may be employed in the catheter 20 of FIG. 1. Here, the electrode structure 240 of the catheter 20 includes an elongated cylindrical conductor 242 formed of metal, such as stainless steel or tungsten, that overlies the carrier 21. The electrode structure 240 further includes an insulator 244 overlying the elongated cylindrical conductor 242. The insulator 244 has a plurality of discrete openings 246 that expose corresponding areas of the elongated cylindrical conductor to the saline within the balloon 26. Each opening 246 forms a corresponding electrode 248. Another electrode 250 forms a common electrode. All of the electrodes 248 and 250 are disposed in non-touching relation to the sidewalls of the balloon 26.

FIG. 4 is a partial sectional view illustrating alternative aspects of the electrode structure 240 of FIG. 3 to provide the plurality of shock wave sources. Here, at least some of the openings 246 are filled with a conductive material to form the electrodes 249. The conductive filler forming electrodes 249 may be of the same material forming the conductive cylinder 242 or may be of a different conductive material. It serves to raise the surface of the electrodes to above the insulator 244 which, in some cases, may result in more reliable arc formation.

Referring now to FIG. 5, it is a side view of another dilating angioplasty balloon catheter 320 including a plurality of shock wave sources according to a further embodiment of the invention. Again, the catheter 320 includes and elongated carrier 321 and an angioplasty dilating balloon 326 at the distal end thereof in sealed relation thereto. The balloon 326 and carrier 321 form a channel 327 through which the balloon may be filled with a liquid, such as water or saline. The carrier 321 also includes a guide wire lumen 329 that is adapted to receive a guide wire 330.

The catheter 320 further includes an electrode structure 340 including a first plurality of electrodes 332 and a second plurality of electrodes 342. The electrodes 332 and 342 are disposed in non-touching relation to the the sidewalls of the balloon 326. During angioplasty treatment, a voltage having a first polarity is applied to the first plurality of electrodes 332 and a reversed polarity is applied to the second plurality of electrodes 342. If the voltage across electrodes 332 and 342 is applied as previously described, an arc will form between corresponding pairs of the electrodes 332 and 342 to produce corresponding shock waves. In this manner, shock waves are produced along the longitudinal dimension of the balloon 326.

It may be seen in FIG. 5 that the electrodes 332 are of larger dimension and have a greater surface area in contact with the saline in the balloon than the electrodes 342. This reduces the impedance to arc plasma formation, allowing the arc plasmas to be produced soon after the voltage is applied to the electrodes. It has also been found that this causes larger arc plasmas to be formed producing stronger shock waves. It still further assists in controlling the electrodes across which the electrical arcs will be produced.

FIG. 6 is a perspective view illustrating a manner in which an electrode structure of the catheter of FIG. 5 may be produced to provide the plurality of shock wave sources according to an embodiment of the invention. In FIG. 6 it may be seen that the electrode structure 340 includes a first conductor 344 and a second conductor 346. The conductors 344 and 346 extend along and within the carrier 321. The conductors 344 and 346 may be made to extend along and within the carrier 321 by co-extruding the conductors 344 and 346 with the elongated carrier during manufacture of the carrier 321. After the extrusion process, openings 348 and 350 may be formed in the carrier 321 to expose corresponding portions of the conductors 344 and 346. This results in the formation of electrodes 332 and 342 respectively. FIG. 7 shows that the openings, such as opening 350 formed in the carrier 321 may be filled with a conductive filler to form electrode 342.

Figure 8:
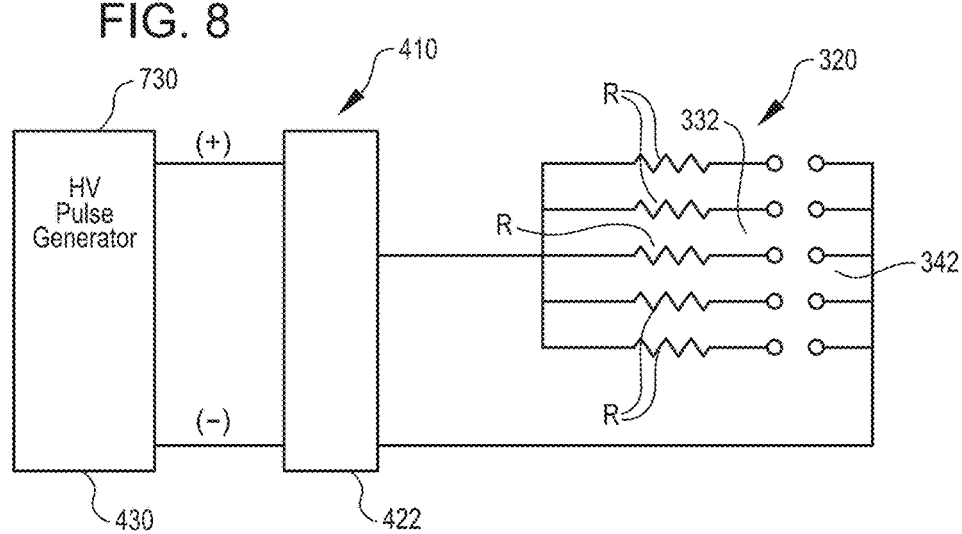
FIG. 8 is a simplified schematic diagram of a shock wave angioplasty system embodying the invention wherein the shock wave source electrodes are arranged in parallel circuit.

FIG. 8 is a simplified schematic diagram of a shock wave angioplasty system 410 embodying the invention wherein the shock wave source electrodes are arranged in parallel circuit. For purposes of this description, the catheter 320 of FIG. 5 shall be used for illustration. The system includes a high voltage generator 430, a connector 432, and a catheter 320. The catheter 320 includes the first plurality of electrodes 332 and a second plurality of electrodes 342. Each electrode of the first plurality of electrodes 332 finds a corresponding electrode in the second plurality of electrodes 342. The connector 422 connects each of the electrodes of the first plurality of electrodes 332 to the plus (+) side of the voltage generator 430 through a resistance R and each of the electrodes of the second plurality of electrodes 342 to the minus (−) side of the voltage generator 430. The resistance R may be provided through individual resistive elements or through resistivity in the conductors that connect the electrodes to the connector and are provided to equalize the current available to each electrode pair. This assures that no one electrode pair will sink all of the available current precluding all other electrode pairs from producing an electrical arc.

Figure 9:
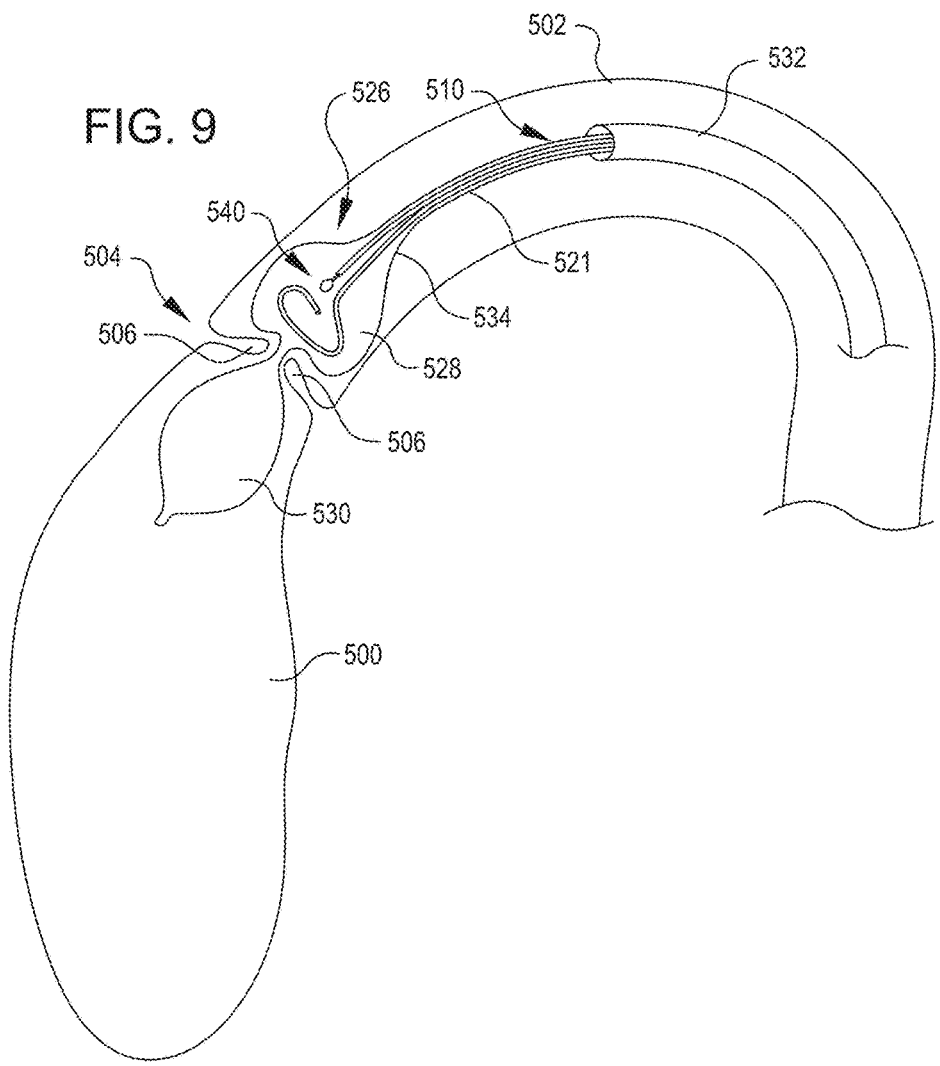
FIG. 9 is a simplified side view of the left ventricle, aorta, and aortic valve of a heart with a valvuloplasty treatment catheter embodying the invention within the aortic valve of the heart.

FIG. 9 is a simplified side view of the left ventricle 500, aorta 502, and aortic valve 504 of a heart with a valvuloplasty treatment catheter 510 embodying the invention within the aortic valve of the heart. The catheter 510 includes a treatment balloon 526 placed on both sides of the aortic valve leaflets 506. Valves of the heart, such as the aortic valve 504 can become stenotic and calcified. More particularly, the opening of the valve defined by the leaflets can become stenotic and calcified. This can restrict the size of the opening as the valve leaflets 506 are thickened with calcium deposits and fibrotic tissue. The thickened leaflets 506 and smaller valve opening restrict blood flow from the heart creating excess work for the heart and poor cardiac output. Current treatment includes replacement of the valve or attempts to stretch the valve annulus with a balloon.

The treatment balloon 526 includes two longitudinally spaced chambers 528 and 530 placed on opposed sides of the aortic valve leaflets 506. The balloon 526 may be formed from a compliant or a non-compliant material. The balloon is at the distal end of a carrier 521. The catheter is placed into position by an elongated delivery tube 532.

The two longitudinally spaced chambers 530 and 528 share a common inflation lumen 534 of the carrier 521 to permit the balloon 526 to be filled with a liquid, such as saline. Alternatively the balloon chambers 530 and 528 may not share the same inflation fluid path.

The catheter 510 includes a plurality of shock wave sources that produce electrical arcs within the balloon to produce shock waves within the confined liquid. The shock waves propagate through the liquid and impinge upon the balloon wall and the valve. The impinging shock waves cause the calcified material on the valve to break and/or soften. This permits the valve opening to be widened or the calcified material to be removed.

In accordance with the embodiment of FIG. 9, the catheter 510 includes an electrode structure 540 within balloon chamber 528. The electrode structure 540 may be seen in greater detail in FIG. 10. The electrode structure generally includes a plurality of electrodes 542 distributed in a path defining a loop and a common or counter electrode 544. The plurality of electrodes may be formed in a manner as previously described by use of an insulated conductor, such as an insulated wire with discrete portion of the insulation removed to form the electrodes. Each of the electrodes 542 forms a shock wave source. As may be seen in FIG. 9, the electrodes 542 are arranged to be in non-touching relation to the sidewalls of the balloon 526.

In use, one polarity, as for example the positive polarity, of the arc forming voltage may be applied to the plurality of electrodes 542. The minus polarity may be applied to the counter electrode 544. Because the electrodes 542 are distributed along the loop as shown, the spacing between the electrodes and the valve will remain essentially constant to enable the entire aortic valve to be treated without diminished shock wave intensities.

Figure 11:
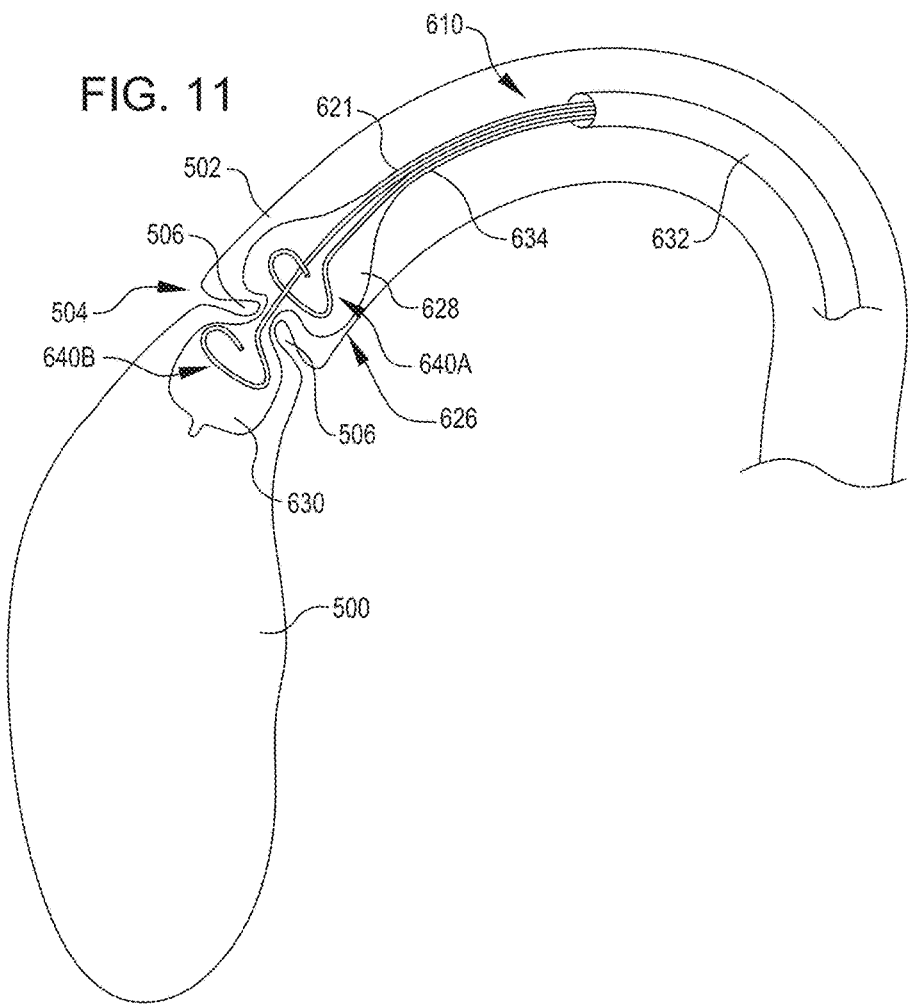
FIG. 11 is another simplified side view of the left ventricle, aorta, and aortic valve of a heart with a dual chamber valvuloplasty treatment catheter embodying the invention within the aortic valve of the heart.

FIG. 11 is another simplified side view of the left ventricle 500, aorta 502, and aortic valve 504 of a heart with another valvuloplasty treatment catheter 610 embodying the invention within the aortic valve of the heart. The catheter 610 includes a treatment balloon 626 placed on both sides of the aortic valve leaflets 506. The treatment balloon 626 includes two longitudinally spaced chambers 628 and 630 placed on opposite sides of the aortic valve leaflets 506. The balloon 626 may be formed from a compliant or a non-compliant material. The balloon is at the distal end of a carrier 621. The catheter is placed into position by an elongated delivery tube 632.

The two longitudinally spaced chambers 630 and 628 share a common inflation lumen 634 of the carrier 621 to permit the balloon 626 to be filled with a liquid, such as saline. Alternatively the balloon chambers 630 and 628 may not share the same inflation fluid path.

Each of the balloon chambers 628 and 630 of the catheter 610 includes a plurality of shock wave sources that produce electrical arcs within their respective chambers of the balloon to produce shock waves within the confined liquid. The shock waves propagate through the liquid and impinge upon the balloon wall and the valve. The impinging shock waves cause the calcified material on the valve to break and/or soften. This permits the valve opening to be widened or the calcified material to be removed.

Figure 10:
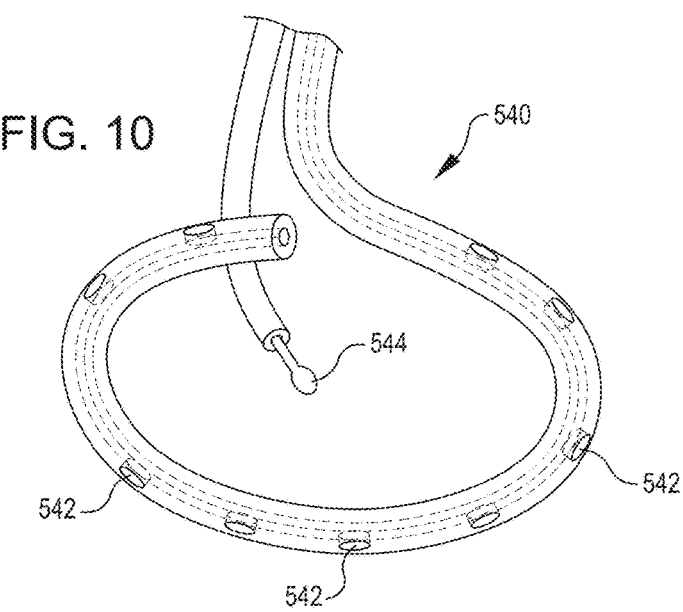
FIG. 10 is a perspective view, to an enlarged scale, of the electrode structure employed in the valvuloplasty catheter of FIG. 9.

In accordance with the embodiment of FIG. 11, the catheter 610 includes an electrode structure 640A and 640B within balloon chambers 628 and 630, respectively. The electrode structures may take the form of electrode structure 540 as shown in FIG. 10. Because the electrodes are distributed in each balloon chamber 628 and 630 along a loop as shown, the spacing between the electrodes and the valve on each side of the valve will remain essentially constant to enable both sides of the entire aortic valve to be treated without diminished shock wave intentsities.

Figure 12:
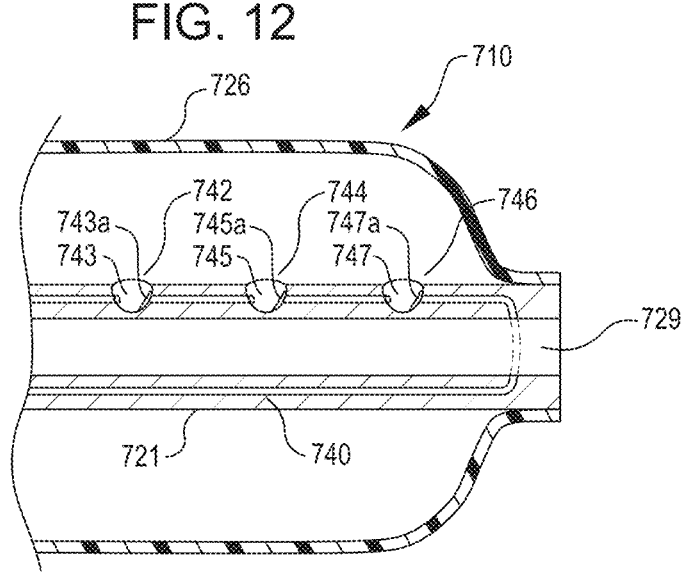
FIG. 12 is a partial side view, to an enlarged scale, of an angioplasty catheter with an electrode structure that may be employed in the embodiments herein wherein the electrodes are arranged in series circuit.

FIG. 12 is a partial side view, to an enlarged scale, of an angioplasty catheter with an electrode structure that may be employed in the embodiments herein, wherein the electrodes are arranged in series circuit. The catheter 710 may be seen to include an angioplasty balloon 726 that is carried at the distal end of an eleongated iunsulative carrier 721 in sealed relation thereto. As in previous embodiments, the carrier has a guide wire lumen 729.

Embedded within the carrier 721 is a conductor 740 that extends to the distal end of the carrier and then back toward the proximal end as shown. At points along the carrier 721 and the conductor 740, portions of the carrier 721 are removed. Corresponding portions of the conductor are also removed. Each removed conductor portion forms a pair of electrodes. For example, removed portion 742 forms an electrode pair 743. Similarly, removed portions 744 and 746 form electrode pairs 745 and 747 respectively. One side of the openings 742, 744, and 746 are coated with a conductive material to render one electrode 743a, 745a, and 747a of each electrode pair larger in surface area then the its other corresponding electrode.

Figure 13:
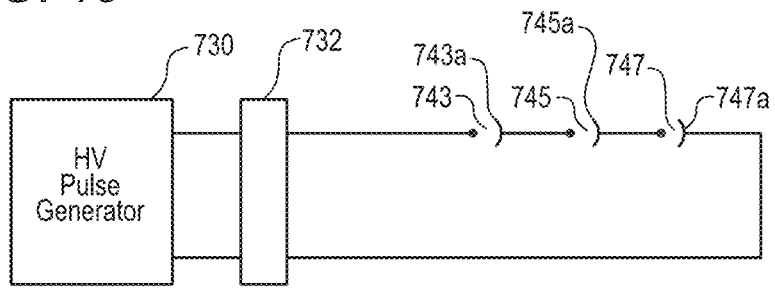
FIG. 13 is a simplified schematic diagram of a shock wave angioplasty system embodying the invention wherein the shock wave source electrodes are arranged in series circuit.

Each of the electrode pairs 743, 745, and 747 forms a shock wave source. As may be noted in FIG. 13, the electrode pairs 743, 745, and 747 are arranged in series circuit. They are connected to a high voltage source 730 through a connector 732. The larger electrode 743a, 745a, and 747a of each electrode pair assures that all of the electrode pairs will reliably arc when the high voltage is applied across the string of shock wave sources.

Figure 14:
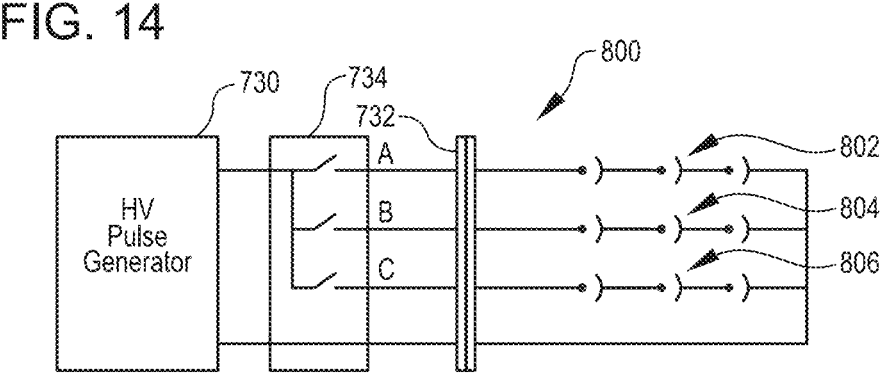
FIG. 14 is a simplified schematic diagram of a shock wave angioplasty system embodying the invention wherein the shock wave source electrodes are arranged in plural series circuits with each series circuit being individually activated.

FIG. 14 is a simplified schematic diagram of a shock wave angioplasty system 800 embodying the invention wherein the shock wave source electrodes are arranged in plural series circuits with each series circuit being individually activated. To that end, the system 800 includes series circuits 802, 804, and 806 of electrode pairs connected to a multiplexer 734 through a connector 732. The multiplexer is arranged to connect a high voltage source 730 across each series circuit 802, 804, and 806 individually, one at a time, or in any combination.

Figure 15:
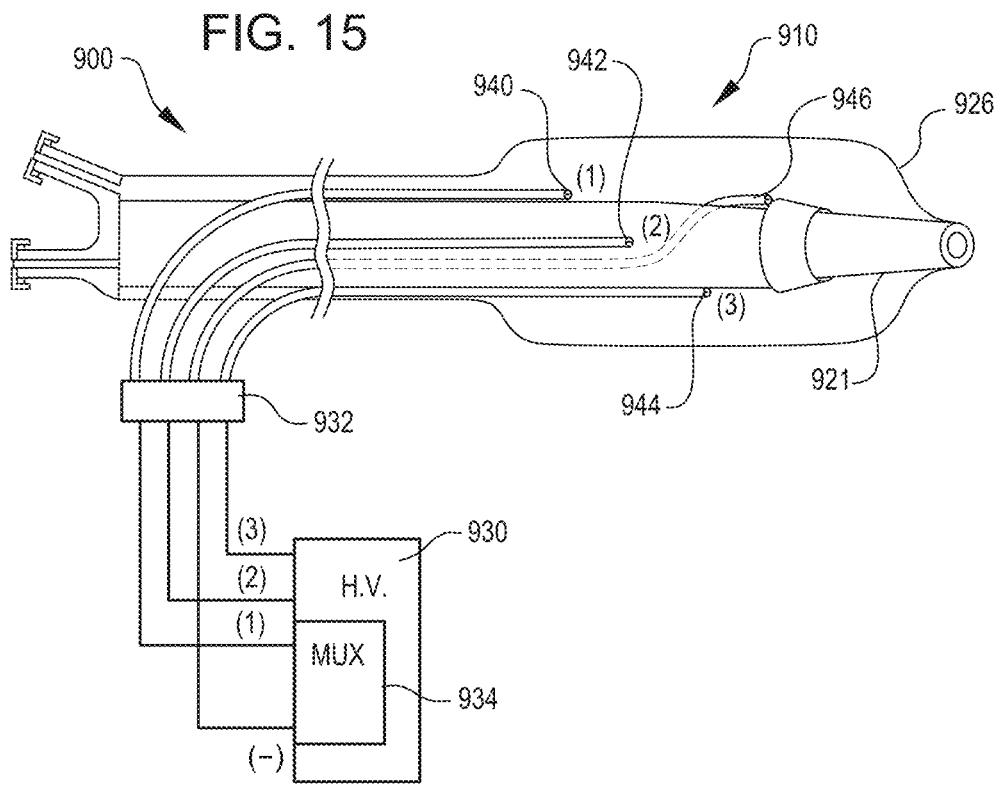
FIG. 15 is a simplified drawing of another angioplasty system embodying the invention including a side view of a dilating angioplasty balloon catheter including a plurality of shock wave sources that are selectably coupled to a power souce, one at a time, according to another embodiment.
Figure 16:
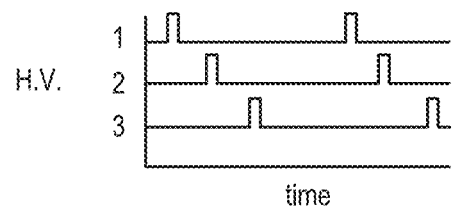
FIG. 16 is a timing diagram illustrating the manner in which the electrodes of FIG. 15 may be selectably coupled to a power source.

FIG. 15 is a simplified drawing of another angioplasty system 900 embodying the invention including a side view of a dilating angioplasty balloon catheter 910 including a plurality of shock wave sources that are selectably coupled to a power source, one at a time, according to another embodiment, and FIG. 16 is a timing diagram illustrating the manner in which the electrodes of FIG. 15 may be selectably coupled to a power source. The system 900 includes a catheter 920, and high voltage power source 930, and a connector 934. The catheter 920 includes an angioplasty balloon 926 carried on a carrier 921 in sealed relation thereto and arranged to be inflated by a liquid, such as saline. The catheter 920 also includes electrodes 940, 942, and 944 carried on the carrier 921 in non-touching relation to the sidewalls of the balloon 926, and a counter electrode 946, also carried on the carrier 921. The electrodes 940, 942, and 944 are each connected to a multiplexer 934 of the high voltage source 930. When an electrode is activated, a high voltage from source 930 is applied across a selected one of the electrodes and the counter electrode to create an electrical arc. The electrical arc causes a plasma to be formed. The creation of the plasma causes a shock wave. Hence, each electrode 940, 942, and 944 forms a shock wave source. The shock waves are propagated through the liquid to impinge upon the balloon sidewall and the calcium deposit to break the calcium deposit up.

As may be seen in FIG. 16, the multiplexer 934 can activate the shock wave sources, one at a time. This reserves all of the high voltage for each shock wave source to thus form shock waves of maximum strength to be applied to the calcium deposits all along the balloon. The shock waves can be of repeatable strength. Longitudinal movement of the catheter to treat the calcium deposits is not required.

While particular embodiments of the present invention have been shown and described, modifications may be made, and it is therefore intended to cover all such changes and modifications which fall within the true spirit and scope of the invention.

We claim:

1. A device for generating shock waves for treating a calcified lesion within a blood vessel or a calcified aortic valve comprising:
   an elongated support;
   a fluid fillable chamber mounted on the support;
   a first wire extending along the support and into the chamber;
   a second wire extending along the support into the chamber, with the proximal ends of the first and second wires being connectable to a high voltage source, and wherein a distal portion of the first wire is helically wound around the support, and wherein a distal portion of the second wire is helically wound around the support, interleaved with the helically wound first wire, the helical windings being located within the chamber, and wherein said first wire is coated with insulation and wherein at least one discrete region of the insulated coating is removed from the side of the first wire opposite to the support to expose said first wire to the fluid in the chamber, said exposed region being in the helically wound portion of said first wire spaced from the distal end thereof and wherein when a high voltage pulse is applied to the first and second wires, an electrical arc is initiated at said exposed region of said first wire allowing current to flow to second wire and generating a shock wave for treating the calcified lesion or valve.

2. A device as recited in claim 1 wherein said first wire includes at least two discrete regions where the insulated coating is removed, each region defining a separate source of shock waves when a high voltage pulse is applied across the first and second wires.

3. A device as recited in claim 2 wherein the second wire is not insulated to define a counter electrode for each of the exposed regions of the first wire.

4. A device as recited in claim 2 wherein the two regions that define separate sources of shock waves are connected in parallel and wherein the high voltage sources includes a resister associated with each region in order equalize the current supplied to the shock wave sources.

5. A device as recited in claim 1 further including a voltage source connected to the first and second wires and wherein said high voltage pulse is between 100 and 3000 volts.

6. A device as recited in claim 1 further including a voltage source connected to the first and second wires and wherein voltage pulse is two microseconds or less.

7. A device as recited in claim 1 further including a voltage source connected to the first and second wires and wherein the voltage pulse is less than one microsecond.

8. A device as recited in claim 1 wherein the chamber is located at the distal end of the support.

9. A device as recited in claim 1 wherein said chamber is a balloon.

\* \* \* \* \*